US009605256B2

(12) United States Patent
Kiss et al.

(10) Patent No.: US 9,605,256 B2
(45) Date of Patent: Mar. 28, 2017

(54) PROCEDURE FOR THE SPECIFIC ISOLATION OF TOTAL DNA CONTENT OF BACTERIAL GERMS AND A KIT FOR THIS PURPOSE

(71) Applicant: Diagon Ltd., Budapest (HU)

(72) Inventors: Gabor Kiss, Szamosszeg (HU); Janos Kiss, Szamosszeg (HU); Katalin Sztancsik Ambrusne Kovacs, Szarvas (HU); Georgina Bernath, Budapest (HU)

(73) Assignee: Diagon Ltd., Budapest (HU)

( * ) Notice: Subject to any disclaimer, the term of this patent is extended or adjusted under 35 U.S.C. 154(b) by 22 days.

(21) Appl. No.: 14/704,580

(22) Filed: May 5, 2015

(65) Prior Publication Data

US 2015/0376601 A1    Dec. 31, 2015

Related U.S. Application Data

(62) Division of application No. 13/808,139, filed as application No. PCT/HU2010/000077 on Jul. 7, 2010, now Pat. No. 9,024,008.

(51) Int. Cl.
*C07H 21/00* (2006.01)
*C12Q 1/68* (2006.01)
*C12N 15/10* (2006.01)

(52) U.S. Cl.
CPC .......... *C12N 15/1003* (2013.01); *C07H 21/00* (2013.01); *C12N 15/101* (2013.01); *C12Q 1/6806* (2013.01)

(58) Field of Classification Search
CPC .............................. C12N 15/101; C07H 21/00
USPC ........................................... 435/6.1; 536/25.4
See application file for complete search history.

(56) References Cited

U.S. PATENT DOCUMENTS 5,576,196 A * 11/1996 Horn .................. C12N 15/1017
435/5

OTHER PUBLICATIONS

Boom et al. Journal of Clinical Microbiology, 1990, pp. 495-503.*

* cited by examiner

*Primary Examiner* — Jezia Riley
(74) *Attorney, Agent, or Firm* — Olson & Cepuritis, Ltd.

(57) ABSTRACT

Procedure for the specific isolation of total DNA content of bacterial germs of different samples, in the course of which the cells are lysated, the DNA content of the lysate is bound selectively, it is washed and then the desalinated linear polymer nucleic acid is eluted from the binding surface in an aqueous solution. Before cell lysis the nonviable bacterial cells are separated from the viable cells on the basis of their different cell surface physical-chemical characteristics, the viable cells of the sample are kept and then lysated using a mechanical and/or enzymatic, favorably lysozyme enzymatic method. After this exclusively double-stranded DNA deriving from the lysate of viable cells is bound on a —$SiO_2$—$TiO_2$— matrix containing chemically activated —OH and dodecylamine groups, and after washing it, the desalinated linear polymer nucleic acid is eluted in an aqueous solution.

5 Claims, 6 Drawing Sheets

Table 1

| BUFFER REMOVING NONVIABLE CELLS | | | |
|---|---|---|---|
| Component | Bottom limit | Top limit | Unit |
| Tris-HCl | 95 | 120 | mM |
| pH | 6.5 | 8,0 | - |
| TRITON X-100 octylphenol ethoxylate | 0.05 | 0,15 | m/m % |
| EDTA | 10 | 20 | mM |
| KCl or NaCl | 10 | 50 | mM |
| citric acid-1-hydrate | 2 | 10 | mM |

Table 2

| LYSIS BUFFER | | | |
|---|---|---|---|
| Component | Bottom limit | Top limit | Unit |
| DTT | 1 | 4 | mM |
| Tris-HCl | 95 | 120 | mM |
| pH | 6.5 | 8.0 | - |
| SDS | 0,3 | 0.6 | mm % |
| EDTA | 1 | 4 | mM |
| TRITON X-100 octylphenol ethoxylate | 0.3 | 0.6 | v/v % |
| NaCl | 40 | 60 | mM |

Figure 4

Table 3

| DNA BINDING MATRIX | | | |
|---|---|---|---|
| Component | Bottom limit | Top limit | Unit |
| SiO2-TiO-OH (-HCl) C12-H25-O-NH | 6 | 14 | g |
| Tris-HCl | 95 | 120 | mM |
| pH | 5.0 | 6.0 | - |
| EDTA | 15 | 25 | mM |
| dextrose or trehalose | 1 | 5 | m/m % |
| BSA | 0.01 | 0.1 | m/m % |
| guanidinium hydrochloride | 5.5 | 6.5 | M |

Table 4

| DESALINATING WASH BUFFER | | | |
|---|---|---|---|
| Component | Bottom limit | Top limit | Unit |
| Tris-HCl | 95 | 120 | mM |
| pH | 6.5 | 8.0 | - |
| EDTA | 15 | 25 | mM |
| NaCl | 5.5 | 6.5 | M |

Table 5

| ELUENT | | | |
|---|---|---|---|
| Component | Bottom limit | Top limit | Unit |
| PCR grade water | - | - | ml |

PROCEDURE FOR THE SPECIFIC ISOLATION OF TOTAL DNA CONTENT OF BACTERIAL GERMS AND A KIT FOR THIS PURPOSE

This application is a division of U.S. patent application Ser. No. 13/808,139, filed on Jan. 3, 2013, now U.S. Pat. No. 9,024,008, which application is a U.S. National Stage of PCT/HU2010/000077, filed Jul. 7, 2010, each of which is incorporated herein by reference.

The subject of the invention is a procedure for the specific isolation of total DNA content of bacterial germs of samples of different origins and a KIT for the realisation of the procedure in practice.

In public health hygienic monitoring of drinking waters, environmental waters, food products, working areas, different communal and environmental surfaces an essential part of microbiological tests of collected samples is the qualitative and quantitative determination of bacterial germs. For such determinations—besides the in vitro culturing on selective or nonselective media and the microscopic detection of them and besides the biochemical reactions elaborated for individual bacterial metabolic steps—now several nucleic acid based molecular diagnostic methods are available too, such as for example polymerase chain reaction (PCR) the in vitro amplification of nucleic acid sequences, or the method of sequencing revealing nucleic acid base sequence, or agarose gel electrophoresis testing the size of nucleic acid fragments obtained [Nucleic Acid Isolation and Purification, $2^{nd}$ Edition, Roche Diagnostics GmbH, 2003]. Unlike traditional techniques, these nucleic acid based molecular diagnostic methods enable analysis even in the case of a small amount of initial samples. The template of these nucleic acid based molecular diagnostic methods is the bacterial nucleic acid in a concentration and purity required by the actual analytical method in use. However, these two parameters, the nucleic acid concentration and purity vary with the preanalytical procedures applied, i.e. with the methods of sample disruption and of nucleic acid extraction. Sample disruption to access template nucleic acids is a multistep process, during which suiting current use the individual steps may take place separately or combined with each other. Traditionally disruption starts with cell lysis, followed by the selective binding-extraction and purification of the target deoxyribonucleic acid (DNA) in the next steps, and then the process ends with the qualitative and quantitative determination of the purified isolated nucleic acid. Disruption can take place while ensuring the appropriate pH, temperature and ionic conditions, mechanically (for example by swelling, ultrasound disintegration, crushing-disruption), chemically (for example with a buffer containing enzymes, surfactants, detergents, ion chelators), in a combined compound of protein denaturing and intracellular desoxyribonuclease inhibiting additives. From the lysate obtained by disruption, the target nucleic acid can be isolated and purified with the help of precipitation-extraction, centrifugation, electrophoresis or chromatography. The semiquantitative analysis of the nucleic acid yield purified from cellular macromolecules and further cellular fragments can take place for example by measuring the fluorescent emission of DNA intercalating polyaromatic stain (e.g. ethidium bromide) induced at ultraviolet wavelength (UV). The quantitative analysis of the isolated nucleic acid can be performed on the basis of the optical density (OD) measured at wavelength $\lambda_{260}$ with UV spectrophotometry. One OD unit corresponds to 50 µg/ml DNA concentration. In order to define the purity of the isolated DNA, the ratio of the optical density measured at two different UV wavelengths ($OD_{260}/OD_{280}$) is used, that is the ratio of light absorption measured at the wavelength characteristic of the aqueous solution of nucleic acids and the aqueous solution of proteins ($\lambda_{260}$ and $\lambda_{280}$). Favourably the value of the $OD_{260}/OD_{280}$ ratio varies in the range between 1.4-2.0. Lower values indicate protein contamination (e.g. residual protein components of the cell lysate), while higher values (>2) indicate spectrophotometric measurement errors or other possibilities of contamination. When using PCR, favourably the $OD_{260}/OD_{280}$ ratio should be between 1.4-1.8.

In traditional everyday public health practice, most commonly bacterial DNA is isolated by using the mixture of phenol-chloroform [Sambrook J. et al.: Molecular Cloning, A Laboratory Manual, Cold Spring Harbor Laboratory Press, 3rd Edition, 2001]. The method is based on that cells are disrupted with lysing buffers containing detergents, protein degrading enzymes, then phenol-chloroform mixture is added to the lysate, as a result of which the acidic phenol phase extracts among others the protein and RNA components of the lysate [Cohn E. J., Conant J. B. (1926): PNAS 12: 433-438.], and the DNA can be isolated with an organic solvent miscible with water, for example with isopropanol [Kirby K. S. (1956): Biochem. J. 64: 405-408.].

The organic solvents mentioned above are undoubtedly efficient in the process of disruption and isolation, but their potential toxic effect threatening laboratory staff and the environment cannot be disregarded. A fairly common solution in avoiding the use of organic solvents mentioned above is when after disrupting biological samples a chaotropic component [Chomczynski P. et al. (1997): Biotechniques 22: 550-553.] is also added to the buffer system isolating genomic DNA content. Due to the chaotropic component denaturating proteins (for example NaJ, KJ, Na-perchlorate, guanidinium hydrochloride—GC, guanidinium thiocyanate—GTC) and the appropriate pH level the nucleic acid associated proteins dissociate, and the functional inhibition of nucleic acid degrading nucleases facilitates efficient DNA isolation. U.S. Pat. No. 4,900,677 describes a procedure suitable for the disruption of both Gram negative and Gram positive bacteria, after which the chromosome DNA content of Pseudomonas aeruginosa and Streptococcus faecalis is isolated, among others, in a quick process using a solution free from organic solvents. In order to extract chromosome DNA, the initial $10^7$-$10^8$ cell mass is disrupted in a Tris buffer pH=8.0 based cocktail containing enzymes with different target spectra (lysozyme, endo-N-acetyl-muraminidase, achromopeptidase, etc.), solubilising (e.g. dimethyl sulfoxide, dimethyl formamide), surfactant (e.g. sodium dodecyl sulfate, TRITON X-100(octylphenol ethoxylate), CHAPS, CHAPSO) and ion chelator (e.g. EDTA) components, by vortex mixing. The contaminating ribonucleic acid (RNA) content is digested with ribonuclease (RNase) enzyme, and the residual enzymatic and non-enzymatic protein content is neutralised by adding Proteinase K. A chaotropic component (e.g.: Na-trifluoroacetate, Na-perchlorate, NaJ) supporting DNA isolation is added to the system, and the DNA obtained in nearly an hour is purified using collodion membrane dialysis. Sample disruption and the neutralisation of residual proteins is further supported with varying reaction temperatures (37°C. and 60°C.). According to U.S. Pat. No. 5,595,876 the neutralisation of residual proteins is also supported by increasing the temperature, in the course of the so-called in situ single tube DNA extraction of Gram negative and Gram positive bacteria.

Avoiding the use of organic solvents in the process of disruption and isolation as described above is successful, but the yield of extraction and the purity of the isolated DNA reduces.

Increasing DNA yield is attempted by an intermediate approach, which supports the selective isolation of DNA by adding a small amount of organic solvent miscible with water in an alkaline buffer medium (e.g.: pH=8-9). In U.S. Pat. No. 5,945,515, in one of the eukaryote examples, from the lysing system also containing a chaotropic component (GTC) in alkaline buffer the RNA content is preliminarily precipitated by adding a small amount of organic solvent, then the precipitate is separated by centrifugation, and by this the DNA to be isolated remains in solution selectively. In further examples of the patent description, in order to accelerate the above DNA isolation, centrifugation steps were reduced in number and then omitted. When analysing the purity of the DNA obtained in this way, contaminating RNA residuals were also detected in agarose gel electrophoresis.

Besides the traditional and intermediate isolation approaches above, in practice other alternative techniques of DNA isolation operating on different principles have become increasingly wide spread for about two decades. In fact one type of these alternative techniques uses the principle of chromatography in the isolation of biological macromolecules [for example the purification of plasmid DNA from lysated *E. coli* using cartridge cassette chromatographic system according to U.S. Pat. No. 6,428,703, or nucleic acid separation on silanised chromatography cartridge according to WO Patent no. 9105606]. These procedures are all based on the idea that after cell lysis the DNA content of the lysate is bound selectively, reversibly on carrier surface. These carrier surfaces can be filters (nitrocellulose, nylon, cellulose acetate, metal oxide), plastic- (PVDF) or glass (silica gel $SiO_2$, $SiO_2$—$TiO_2$) based matrixes [Boom R. et al. (1990): J. Clin. Microbiol. 28: 495-503., Mackey K. et al. (1998): Mol. Biotechnol. 9: 1-5., Boom R. et al. (1999): J. Clin. Microbiol. 37: 615-619., Dames S. et al. (2006): J. Mol. Diagn. 8: 16-21., Gushikem Y., Rosatto S. S. (2001): J. Braz. Chem. Soc. 12: 695-705.], or maybe microparticles and beads obtained by combining different ions and polymers, during the use of which the steps of disruption and DNA extraction can be automated [Youngman L. D. et al. (2002): Clin. Chem. 48: 1629-1630., Smith K. et al. (2003): J. Clin. Microbiol. 41: 2440-2443.]. WO Patent no. 2004033707 describes the use of Na-silicate carrier, WO Patent no. 2004046231 describes the use of silica, silica gel bound to polypropylene, polystyrene, polycarbonate carrier (tube, microplate well) in the course of the isolation of eukaryotic mitochondrial DNA (mtDNA) or total blood DNA content. In the single step method described in WO Patent no. 1998023630 the role of the hydroxylated aromatic hydrophobic polymer, polyhydroxystyrene is described in retaining the contaminating components of the cell lysate, while nucleic acid leaves with the eluent. WO Patent no. 2002000930 describes DNA extraction from faeces smear sample applied on a nylon or guaiac impregnated carrier, with the help of guanidinium salt, while in US Patent no. 20080319182 DNA binding is ensured by providing a special cationic surface. Nucleic acids, including DNA, bind on the surface of these carriers under unique physical-chemical circumstances (temperature, centrifugal force, electrolyte conditions, etc.), with reversible secondary bonds and with selectivity characteristic for the carrier. After removing the carrier with the DNA bound on its surface from the solution and after appropriate desalination, the bound DNA can be isolated by eluting it from the carrier.

For downstream molecular applications (e.g. PCR, enzymatic digestion, sequencing, electrophoresis, etc.) the most important parameters of the isolated DNA are purity (see below), quantity (concentration μg/ml) and the integrity/fragmentation i.e. the physical maintenance of the molecule.

The advantage of the traditional extraction methods with organic solvents mentioned above is the relatively satisfactory purity ($OD_{260}/OD_{280}$ index=1.4-1.7) and large concentration (>50 μg/ml). Their disadvantage is that the residual solvents may disturb the sensitive downstream molecular applications (e.g. hydrolysis probe directed real-time PCR, microarray), and that the isolation procedure is time consuming (min. 1.5-2 hours). In respect of their efficiency these procedures have poor reproducibility, the combined variance between two independent isolations (CV %) is high, so they are difficult to adjust to standard laboratory protocols.

The alternative techniques and reagents based on the selective binding of DNA from a solution using carriers listed above have better technical parameters, their reproducibility index is better, they operate according to a slightly faster protocol, and due their standardised nature they are easier to adjust to instrumental isolation methods.

U.S. Pat. No. 5,234,809 describes a nucleic acid isolation procedure, among others, with the use of which both single-stranded and double-stranded DNA can be isolated. In the course of the described procedure the target nucleic acid is isolated without preliminary lysis, from the complex biological sample itself (e.g. total blood, blood serum, urine) in such a way that in the single tube buffer system the ion chelator (e.g. EDTA) binding divalent ions, the chaotropic compound (e.g. GTC) precipitating protein molecules from their solution and the matrix surface (e.g. silica, or latex particles, or nitrocellulose filter) binding target nucleic acids are all in the same reaction space. In the case of bacterial samples the result of the procedure is significantly influenced by the initial cell concentration, so the size range of silica particles of nucleic acid binding matrix varies per application.

WO Patent no. 9534569 contains a further example of cell disruption and DNA isolation in the same reaction space, in the course of which the significantly contaminated small sample (e.g. $5 \times 10^3$ cells, 0.5 μl blood) is lysated in the same microplate well, in which the DNA content is extracted on a non-porous, disperse, homogenous matrix surface consisting of 40 nm $SiO_2$ particles. The size of the DNA isolated in the course of the procedure varies in the range between 50 nucleotides-60,000 nucleotides. Similarly, DE Pat. No. 4,422,044 also describes cell disruption and DNA isolation in the same reaction space, in the course of which the DNA content of bacterial plasmid, or HeLa cell cultures is isolated with similar efficiency from the same small amount of initial sample as above.

An advantage of the same reaction space above is the minimisation of technical contamination (e.g. pipetting). However, it cannot be disregarded that in this common reaction space, besides nucleic acid molecules to be isolated, further components (e.g. lipids, single-stranded nucleic acids, pigments, small molecules) as potential inhibitors of downstream applications (e.g. PCR) may also be absorbed or bound on matrix surfaces. The removal of these potential downstream inhibitors requires further separate steps in the process of nucleic acid isolation. Due to this, the elution of nucleic acids bound to silica based carriers listed above with an eluent also containing ion chelator is preceded by several times washing with buffer and organic solvent. As mentioned earlier, fundamental issue of DNA isolation is the maintenance or integrity of the molecule during the whole process. The mechanical effects applied, such as pipetting, mixing, centrifugation, as well as the contacts with different detergent, ion chelator and chaotropic components may result in distortions or even fractures in the structure of nucleic acids. The realisation of cell lysis and nucleic acid isolation in the same reaction space as described above, minimising the necessity of centrifugation all offer possibilities for the increased maintenance of DNA integrity. At the same time, besides DNA integrity, the purity and yield of nucleic acid required by downstream molecular applications cannot be disregarded. Following this complex aim, unlike single space methods, in our procedure according to the invention we perform cell lysis and then selective DNA isolation in separate reaction spaces, as a result of which the steps of washing become simpler, the DNA isolate is produced in about 30 minutes, its purity according to the $OD_{260}/OD_{280}$ ratio (1.8 on average) and its yield (20-100 µg/100 mg initial sample) is favourable for PCR and other downstream molecular applications. In our procedure according to the invention, for the selective binding of bacterial double-stranded DNA a —$SiO_2$—$TiO_2$— matrix with increased chemical and thermal stability is created, on the surface of which there are chemically activated —OH (silanol, titanol) and dodecylamine groups, and which have been favourably preliminarily cross-linked with dodecylamine linkers.

U.S. Pat. No. 6,787,307 provides a solution for nucleic acid isolation, bacterial chromosome DNA, plasmid DNA extraction with a matrix surface consisting of magnetised silica particles. In the method described, by using the appropriate magnetic field the magnetised silica particles can be easily separated together with the nucleic acid binding to their surface, to be isolated from the lysate. In the above isolation step, besides target DNA molecules of the lysate produced by cell disruption, further cell components, the inhibitors of downstream applications (e.g. PCR), also become adhered to the matrix surface. The removal of these latter components is a time-consuming multi-step process (see above). Unlike this, in our procedure according to the invention, no PCR inhibitors adhere to the DNA binding matrix surface created by us.

According to one of the realisations of US Patent no. 20100021905, DNA-RNA mixture of mammalian tissue origin is bound to a silica-based matrix surface, under buffer circumstances supporting the binding of both nucleic acids. The bound DNA is eluted in an alkaline reagent (pH=10) separately from the proteins and the RNA. The selectivity of the procedure increases in proportion with the guanidinium salt anion size, so according to the teaching of the description, instead of chloride ions the presence of thiocyanate ions is more favourable for the efficient extraction of DNA. In the chaotropic support of DNA isolation on the carrier according to our invention, —$SiO_2$—$TiO_2$— matrix surface, guanidinium hydrochloride also proved to be favourable.

The difficulties of the known alternative techniques may be first of all due to that
  a) if they are able to isolate DNA with great selectivity, then the pure DNA yield free from components inhibiting downstream molecular applications (e.g. PCR), remains below 20 µg of total isolatable DNA, or
  b) if greater DNA yield is possible (20-100 µg/ml), then the purity of the obtained DNA is rather questionable, that is the $OD_{260}/OD_{280}$ ratio is low (1.3-1.4).

Furthermore, the alternative techniques are generally characterised by that
  a) in most cases the selectivity and quantity parameters of nucleic acid binding to the carrier are questionable, that is apart from the double-stranded DNAs intended to isolate they also bind single-stranded DNAs and RNAs, and the presence of these latter may distort or disturb downstream molecular applications and molecular specificity,
  b) the amount of the isolated DNA significantly depends on the binding ability of the carriers,
  c) the quality and inhibitor content of the isolated DNA significantly depends on the sample,
  d) they are efficient mostly in the case of selectively enriched microbial samples, they are not so efficient in isolation from complex or mixed bacterial samples,
  e) most importantly, nearly all isolation techniques extract DNA of both viable and nonviable bacterial cells, and chromosomal DNA deriving from nonviable cells generate false positive signals in the course of detection procedures.

In respect of the chemicals and reagents trade, in current practice there is no DNA preparation procedure fulfilling all of the following requirements at the same time:
  a. it can be performed reasonably quickly even in the case of general laboratory infrastructural backgrounds,
  b. it isolates total DNA exclusively from live cells, that is it provides a dynamic result,
  c. it provides a significant result even in the case of appropriately low number of microbial germs,
  d. it is specific only to double-stranded DNA,
  e. it is suitable for obtaining DNA of appropriately high chemical purity (without inhibitors) and in an appropriately high concentration,
  f. it can be characterised with favourable reproducibility and a low number of combined variance,
  g. collected microbial samples are possible from many different sources.

The aim of the procedure according to the invention is to eliminate the disadvantageous features of the known techniques and to elaborate a preparative process, in which the specific isolation of total DNA content of bacterial germs has the advantages included in points a.-g. and can be introduced as a reliable validated method in microbiological diagnostic practice (public health, clinical practice, water and food hygiene).

It can be seen on the basis of the examples described above that none of the cell disruption and nucleic acid extracting procedures of the preanalytical phase preceding bacterial nucleic acid-based molecular diagnostics deals with the separation of viable and nonviable cell populations of the initial samples. Making a distinction between the two latter cell conditions may significantly influence the result of isolating bacterial total DNA content and also downstream molecular applications.

Similarly to eukaryotes, the dynamics of bacterial cell populations are also regulated by cell proliferation and cell death influenced by extracellular and intracellular factors. For this reason, when isolating bacterial total DNA content of public health hygiene samples the phenomenon of cell death is a factor that cannot be neglected.

In biological systems a type of cell death is necrosis, that is cell damage induced by physical and/or chemical and/or biological effects, which is a process that can be described for example by the increased passive permeability of cell membrane and cell wall, the disintegration of cell components, the dissociation of cellular organisation and escaping of the cell content, generally by the degradation of the cell [Robbins and Cotran Pathologic Basis of Disease: 8th edition, Saunders, Elsevier, 2010], in which process the decomposition products deriving from the necrotising cell have toxic effects on others in the neighbourhood. In biological systems another type of cell death is apoptosis, that is programmed cell death well defined in eukaryotes [Diaz L. F. et al. (2005): Cell Death and Differentiation 12: 1449-1456.]. This latter type of cell death is an active process under genetic control influenced by environmental stimuli (e.g. morphological rearrangements accompanying changes in metabolic activity of distinct periods in ontogeny), in the course of which due to the structural changes of the cell membrane (e.g. loss of phosphatidylserine asymmetry, modification of transport processes) the adhesion ability and turgor of the cell decreases, and shrinking of the cell appears along with intracellular enzymatic cleavages, in the course of which the DNA content becomes fragmented, and at the end of the process the cell that has undergone apoptosis is utilised by others in the neighbourhood. An increasing number of data relates to the role of apoptotic mechanisms in the so-called adaptation to environmental stress of procaryotic populations [Lewis K. (2000): Microbiol. Mol. Biol. Rev. 64: 503-514, Koonin E. V., Aravind L. (2002): Cell Death and Differentiation 9: 394-404.]. An example for this is the sporulation of the Gram-positive genus *Bacillus* or *Streptomyces* and the Gram-negative Myxobacteria, which drives the cell into programmed cell death with autolysin enzymes induced in the mother cell. The adaptive appearance of non-culturable mutations in numerous Gram-negative bacteria can also be mentioned here as an example [Hochman A. (1997): Critical Rev. Microbiol. 23: 207-214.].

For the isolation of total DNA content of bacterial germs of public health hygiene test samples, a prior step to separate viable and nonviable cell populations is of diagnostic significance. Consequently a further aim of our procedure according to the invention is to elaborate a cell separation procedure ensuring the separation of viable and nonviable bacterial cells and supporting the isolation of total DNA content exclusively from viable cells.

The criteria of cell death described above may explain our observation, according to which in our test samples necrotic complexes appear on the surface of nonviable bacterial cells, which complexes result in the aggregation of this cell population. We also observed that hydration of nonviable cells changes, their lower suspensibility is different from the suspensibility of viable cells, and the cell surface to cell volume proportions also change. We realised that on the basis of the above physical-chemical characteristics viable and nonviable bacterial cells can be distinctly separated, if a solution containing a buffered mixture of appropriate detergent and electrolyte, favourably TRITON X-100 (octylphenol ethoxylate), ethylenediaminetetraacetic acid, KCl or NaCl, citric acid-1-hydrate, that is our so-called buffer removing nonviable cells is used, and the cells are sedimented by changing the centrifugation field strength influencing sedimentation. We presumed that as a result of the change in the hydration of the necrotised bacteria, the cell surface, the cell volume, that is the cell size and density will also change, which, together with the appropriately chosen field strength, is a differentiating factor during sedimentation by centrifugation.

When studying examples of eukaryotes, the separation of viable and nonviable cells by centrifugation at an appropriate field strength takes place on the basis of the cell size and density/hydration. As a result of this the nonviable cell mass appears in the supernatant, while the viable cell mass appears in the sediment [Fisher D. et al.: Cell Separation: A Practical Approach, Oxford Univ. Press, 1998.]. However, it must be considered that even at corresponding centrifugation field strengths the separation is often incomplete, and a small amount of viable cells can also be detected in the supernatant. A further opportunity of separation supplementing the above is density gradient centrifugation used for the separation of cells with different sizes and densities, and, if necessary, a further supplementary separation solution may be the in vitro cultivation of the individual sedimentation fractions. The series of separation steps described above is obviously time-consuming and during these separation steps the chances of cell loss accumulate, reducing the precision of a downstream application. However, the maintenance of cell mass of the initial test sample is essential in the separation of viable and nonviable cells for the specific isolation of total DNA content of exclusively viable bacterial germs.

On the basis of the above, in our procedure the distinction of viable and nonviable cells is based on the different cell sizes characteristic of the two cell conditions, and on their different permeability and hydration due to the structural transformation and changed ionic affinity of the cell membrane. The distinction made according to our procedure was checked with the help of a flow cytometer device.

The use of the flow cytometer is based on that a hydrodynamically focused cell suspension is passed through a monochrome laser beam in such a way that the cells passing by the detection window one by one at a given time scatter light forwards and sideways suiting their size and internal organisation (forward scatter—size) (side scatter—internal organisation), and the light is forwarded to the detectors by an optical system. The signs arriving at the detectors are summarised by the apparatus electronically and displayed in the form of a scatterogram or histogram (bell curve). In our case cell size is taken as a basis for making a distinction between viable and nonviable cells (see the description). The scatterogram and the histogram indicate the amount of cells that can be allocated to the given cell size, so it is obvious for a specialist skilled in the art that flow cytometry is suitable for the instrumental quantitation of viable and nonviable cell populations of the sample under study [Shapiro H. M.: Practical Flow Cytometry, 2nd Edition, John Wiley & Sons, New York, 1988].

Figure 1A:
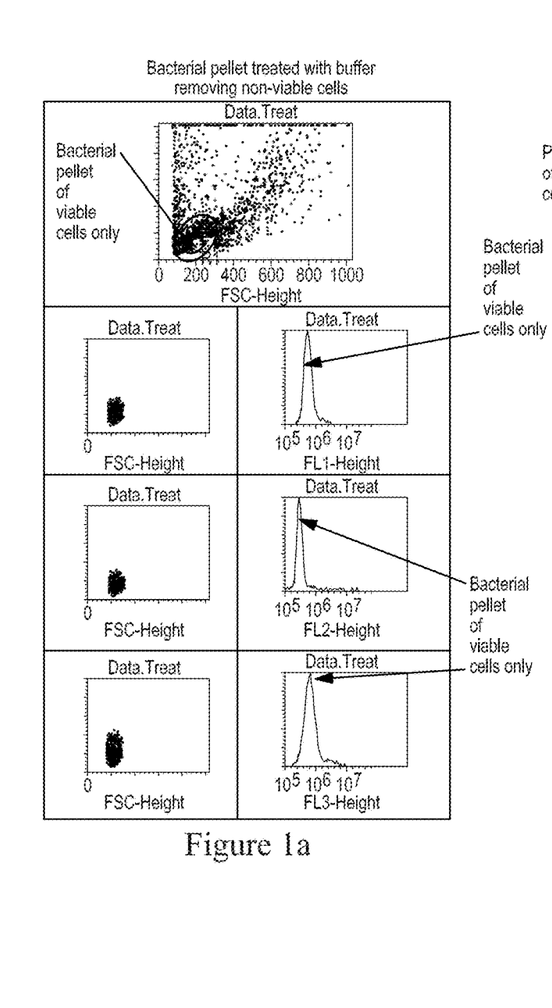
FIG. 1a is a flow cytometry scatterogram (points) and histogram (bell curves) of sediment fraction obtained by centrifugation of bacterial cells treated with a buffer for removing nonviable cells.
Figure 1B:
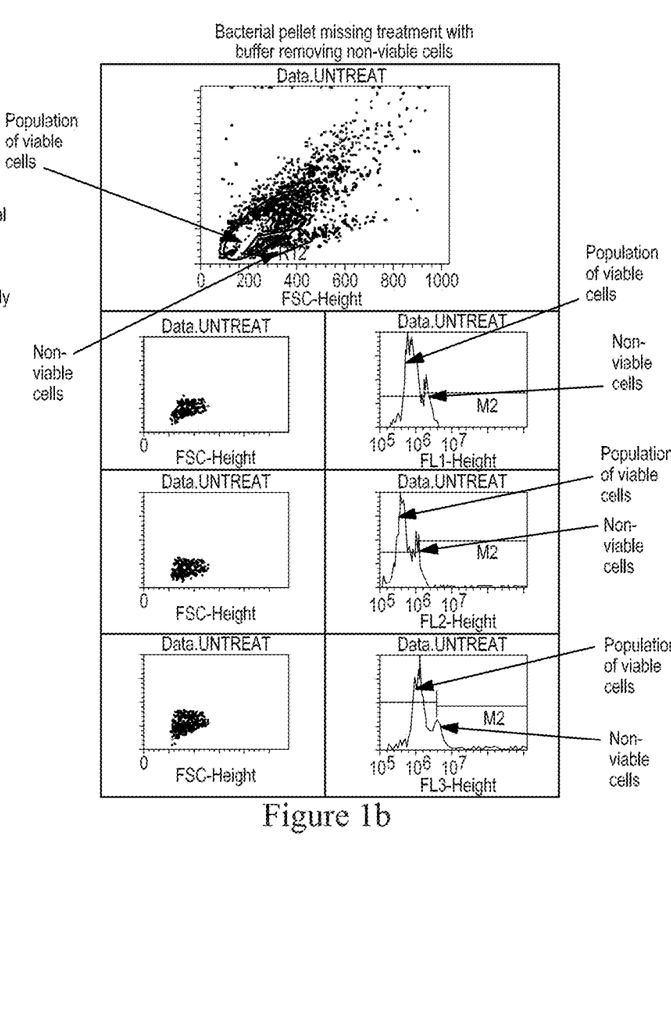
FIG. 1b is a flow cytometry scatterogram (points) and histogram (bell curves) of sediment fraction obtained by centrifugation of bacterial cells not treated with a buffer for removing nonviable cells.

We realised that after washing the sample repeatedly several times with our buffer removing nonviable cells and after centrifugation under given circumstances, the nonviable cells remain in the supernatant, while viable bacterial cells can be selectively sedimented and forwarded for DNA isolation. We proved and validated our recognition with flow cytometry detection described above when we checked the presence of viable and nonviable cells in the sediment and in the supernatant. Our results are summarised in FIG. 1 in scatterograms and histograms of 1a. and 1b. (for detailed explanation see the description of the figure).

At this point, with the sediment containing viable cells separated from the test sample treated with buffer removing nonviable cells developed by us, the process of DNA isolation can be started (lysis, DNA binding, washing, eluting).

During our experiments we succeeded in developing a double-stranded DNA binding carrier matrix, with which exclusively double-stranded DNAs are bound directly and selectively following cell lysis, without the contaminating inhibitor components of the lysated sample. In our double-stranded DNA binding carrier matrix the use of —$SiO_2$—$TiO_2$— matrix containing chemically activated —OH and dodecylamine groups is favourable. It is especially favourable, if the activated dodecylamine groups are preliminarily cross-linked with dodecylamine linkers. With this cross-linked matrix, conditions for target binding specific reaction are created while inhibiting the binding of contaminating and residual inhibitor components of complex samples (blood, faeces, soil).

Figure 2:
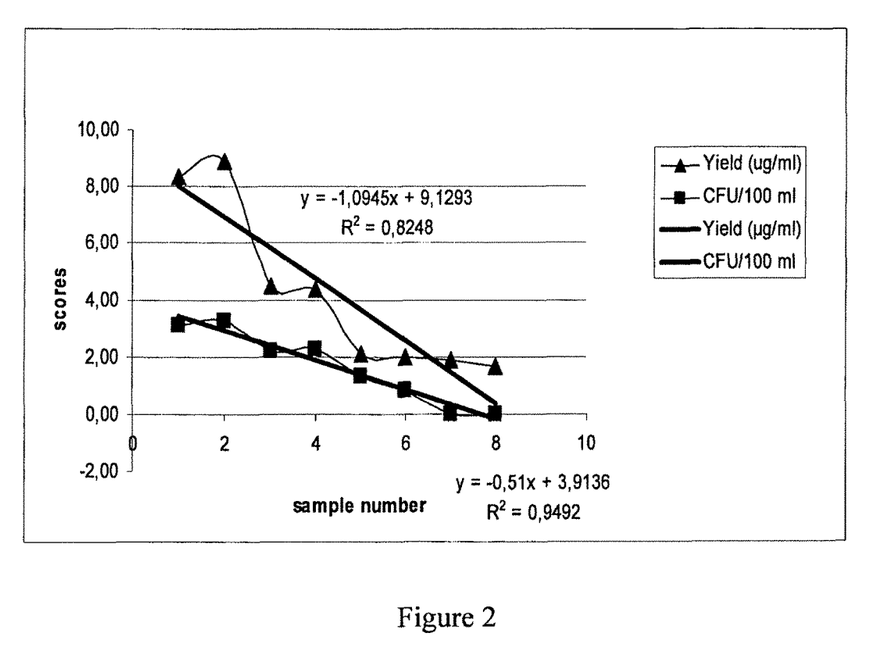
FIG. 2 is a graphical representation of DNA yield from an amount of colony forming units (CFU) present in water samples of *Legionella pneumophila* at different dilutions.

The sensitivity of our procedure was demonstrated by the selective isolation of total DNA content of thin test samples with low CFU (colony forming unit) titer (see FIG. 2 and its detailed explanation).

The subject of our invention is a procedure for the specific isolation of total DNA content of bacterial germs of different samples, in the course of which the nonviable cells are removed, the maintained viable cells are lysated, from the lysate the total DNA content is bound selectively, the bound total DNA content is washed and desalinised, and then the desalinated nucleic acid is eluted from the binding surface in an aqueous solution. By sample we mean public health hygiene test materials such as water, food, clinical, solid and liquid environmental materials, as well as liquid trapped air, the bacterial cell population of which is treated with our buffer removing nonviable cells directly after sampling or before enrichment, preceding lytic disruption. The essence of using our buffer removing nonviable cells is that nonviable and viable bacterial cells are distinguished on the basis of their different cell surface physical-chemical characteristics, as a result of which double-stranded DNA deriving exclusively from the lysate of viable cells is bound on DNA-binding carrier matrix, favourably —$SiO_2$—$TiO_2$— matrix containing chemically activated —OH and dodecylamine groups, favourably cross-linked with dodecylamine linkers preliminarily. On DNA-binding carrier matrix nonspecific secondary links are blocked by adding trehalose or dextran, and BSA.

In the case of a favourable realisation of the procedure the viable and nonviable bacterial cells are distinguished on the basis of their different cell surface permeability and ionic affinity listed above.

In the case of a further favourable realisation of the procedure a differently penetrating wash solution is used for distinguishing viable and nonviable bacterial cells. For example a wash solution containing detergent, electrolyte, favourably Triton X-100, ethylenediaminetetraacetic acid, KCl or NaCl, citric acid-1-hydrate in a buffered mixture (for composition see FIG. 4-table 1) is used, and the field strength of centrifugation influencing cell sedimentation is changed.

In our procedure the lysis of viable bacterial cells is performed with mechanical disruption or combined mechanical and enzymatic disruption, the latter favourably being lysozyme digestion, in uniquely prepared destruction tubes. The mechanical disruption of the bacterial cells is supported with the use of a bench-top device.

Practically, in our procedure according to the invention, the double-stranded DNA content of at least $10^4$ CFU/ml bacterial sample is isolated with a lysis buffer containing redox component, chelating agent and detergents, favourably dithiothreitol (DTT), ethylenediaminetetraacetic acid (EDTA), TRITON X-100 (octylphenol ethoxylate) and sodium-dodecyl-sulphate (SDS). Contaminating colouring substances deriving from the viable bacterial cells and further PCR inhibitors (porphyrins, haem compounds, polyaromatic materials) are separated during the sedimentation of the bacterial lysate, because the lysis buffer also provides favourable physical-chemical environment for the precipitation of these materials.

In the case of a very favourable realisation of the procedure according to the invention, the degradation-free selective binding of the double-stranded DNAs deriving from the lysate of viable bacterial cells is performed on a —$SiO_2$—$TiO_2$— matrix (for composition see FIG. 5—table 3) containing chemically activated —OH and dodecylamine groups, which matrix is preliminarily cross-linked with dodecylamine linkers. On the matrix nonspecific secondary links (RNAs, proteins, other macromolecules) are blocked by adding trehalose or dextran, and BSA.

The quantity and quality (purity) of the isolated double-stranded DNA is checked with a UV spectrophotometer at a wavelength of 260 nm and 280 nm, and the $OD_{260}$ and $OD_{280}$ extinction values are compared. The semiquantitative quantity test is conventional agarose gel electrophoresis following the in vitro PCR amplification of the isolated DNA (for an example see FIG. 3 and its detailed explanation).

The invention also relates to a KIT suitable for extracting total DNA content of bacterial germs for the realisation of the procedure described above, which is first of all for the purpose of analysing water, food, different communal surfaces and public health samples. The structural image of the composition of the KIT can be seen in FIG. 6 (for the detailed explanation see the description of the figure).

Below the figures are explained in detail.

FIG. 1. Demonstrating the efficiency of the removal of nonviable cells before the isolation of total DNA content of bacterial germs, with the help of flow cytometry. Axis x indicates the cell size, while axis y indicates the cell quantity that can be allocated to the given size. FIG. 1a. shows the flow cytometry scatterogram (points) and histogram (bell curves) of the sediment fraction of bacterial cells after centrifugation—treated with buffer removing nonviable cells prepared by us (for buffer composition see FIG. 4—table 1).

FIG. 1b. shows the flow-cytometry scatterogram (points) and histogram (bell curves) of the sediment fraction of bacterial cells after centrifugation—not treated with buffer removing nonviable cells. On comparing the two figures, it can be seen that according to FIG. 1a. the viable, isodiametric, hydrated cells can be sedimented in a homogenous fraction (referred to as "pellet" in the figure), while slightly or not at all hydrated necrotic cells remain in the supernatant as a result of treatment with buffer removing nonviable cells.

According to FIG. 1b. when sample cells are not treated with buffer removing nonviable cells the composition of the sediment (pellet) is heterogeneous, and a further additional fraction appears beside the viable cells; the histogram is falsely extended.

FIG. 2. Isolation of total DNA content of bacterial germs according to our procedure from an aqueous sample with low CFU titer (CFU/100 ml), comparing the logarithmic values of the cell quantity (axis y, lower curve with quadrangles) that can be allocated to the sample numbers (axis x) and the isolated DNA yield (axis y, upper curve with triangles). Total DNA content of bacterial germs was isolated from water samples of different dilutions, that is different CFU titers (axis y, lower curve with quadrangles) of *Legionella pneumophila*. The flow of the regression line of bacterial DNA yield (μg/ml) obtained by our isolation procedure and of the initial cell number is similar, but in the case of DNA yield there is a greater slope. On the basis of the similar flow of the regression lines it can be concluded that bacterial total DNA isolation by our procedure reliably follows the initial cell quantity. The fact that DNA can be favourably isolated (μg/ml values on the upper curve of axis y allocated to sample numbers 5-8 on axis x) even in the case of the greater slope of the regression line of DNA yield and in the case of significant dilution (CFU values on the lower curve of axis y allocated to sample numbers 5-8 on axis x) drives us to the conclusion that double-stranded DNA isolation according to our procedure is also reliable in the case of a low titer of cells, that is in great dilution. Consequently the DNA isolation according to our procedure proved to be sensitive.

Figure 3:
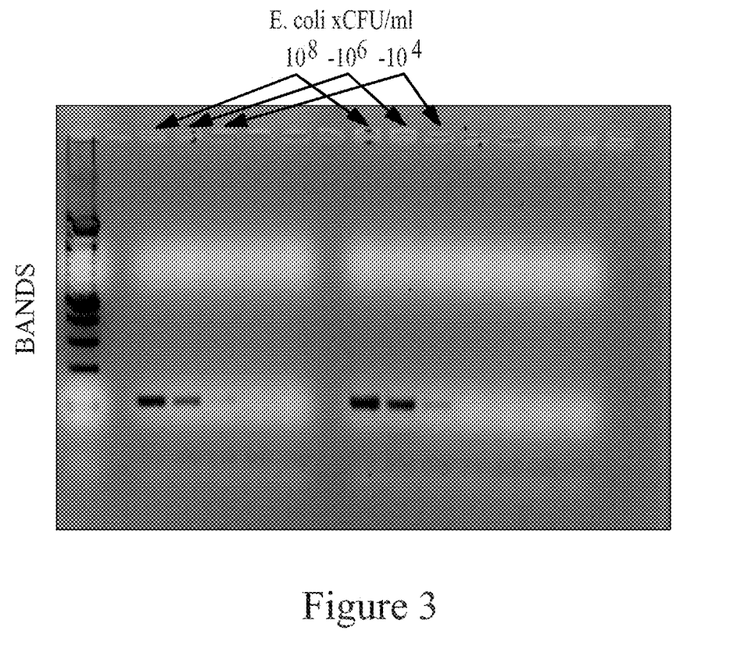
FIG. 3 shows results of agarose gel electrophoresis *E. coli* samples treated in accordance with the present invention.

FIG. 3. Semiquantitative analysis of bacterial total DNA isolated with our procedure according to the invention, in the example of *E. coli*, with agarose gel electrophoresis. In the course of semiquantitative procedure first DNA free from inhibitors, eluted from the matrix surface is entered into a PCR reaction, next the multiplied polynucleotide is analysed with agarose gel electrophoresis using DNA-intercalating stain ethidium bromide for fluorescent emission induced by UV excitation. On the basis of the density bands seen in the figure, the sensitivity threshold of our isolation procedure is $10^4$ CFU/ml. In the extreme left column of the agarose gel the molecular weight reference polynucleotide electrophoregram can be seen, the other columns show the electrophoretic image of the PCR amplified product of total DNA isolated from *E. coli* of water sample. The DNA isolations from bacterial titers of $10^8 \times$CFU/ml; $10^6 \times$CFU/ml; $10^4 \times$CFU/ml shown at the top of the columns took place in 10 independent repetitions.

Figure 4:
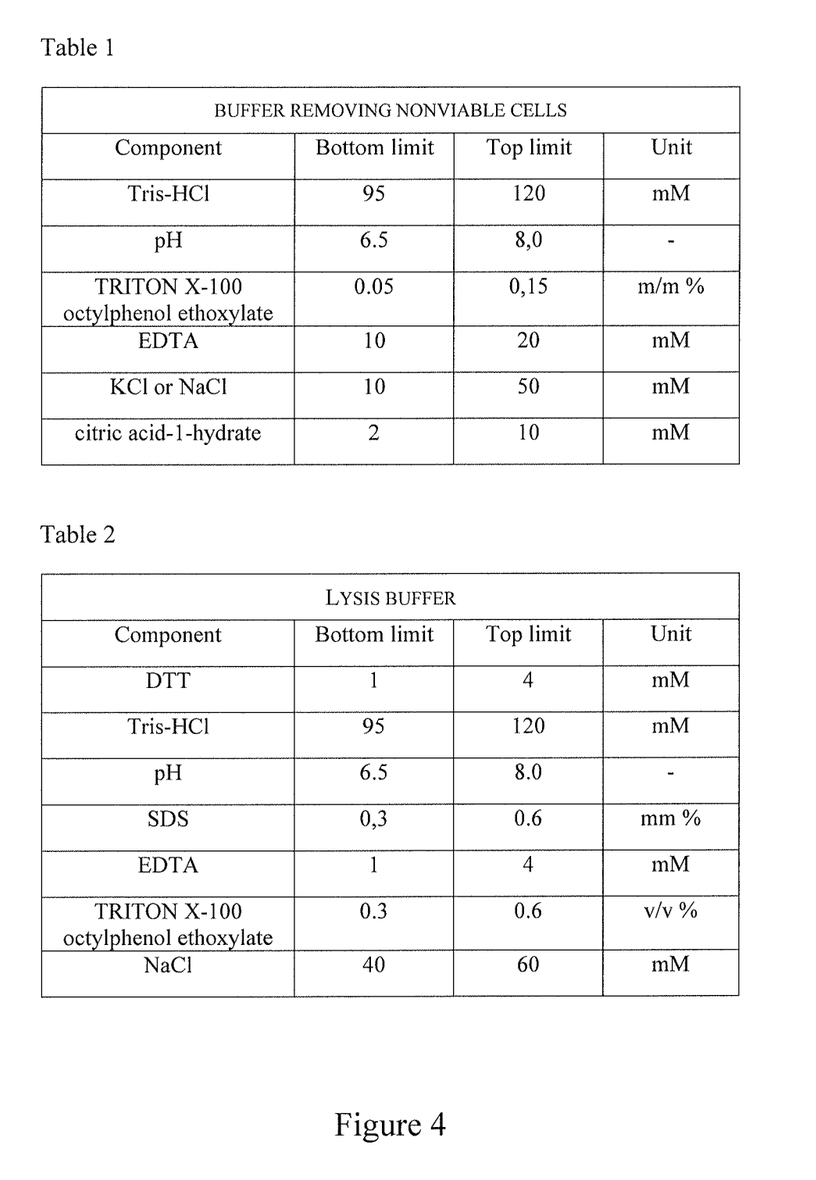
FIG. 4 shows compositions of a buffer for removing nonviable cells (Table 1) and a lysis buffer (Table 2)
Figure 5:
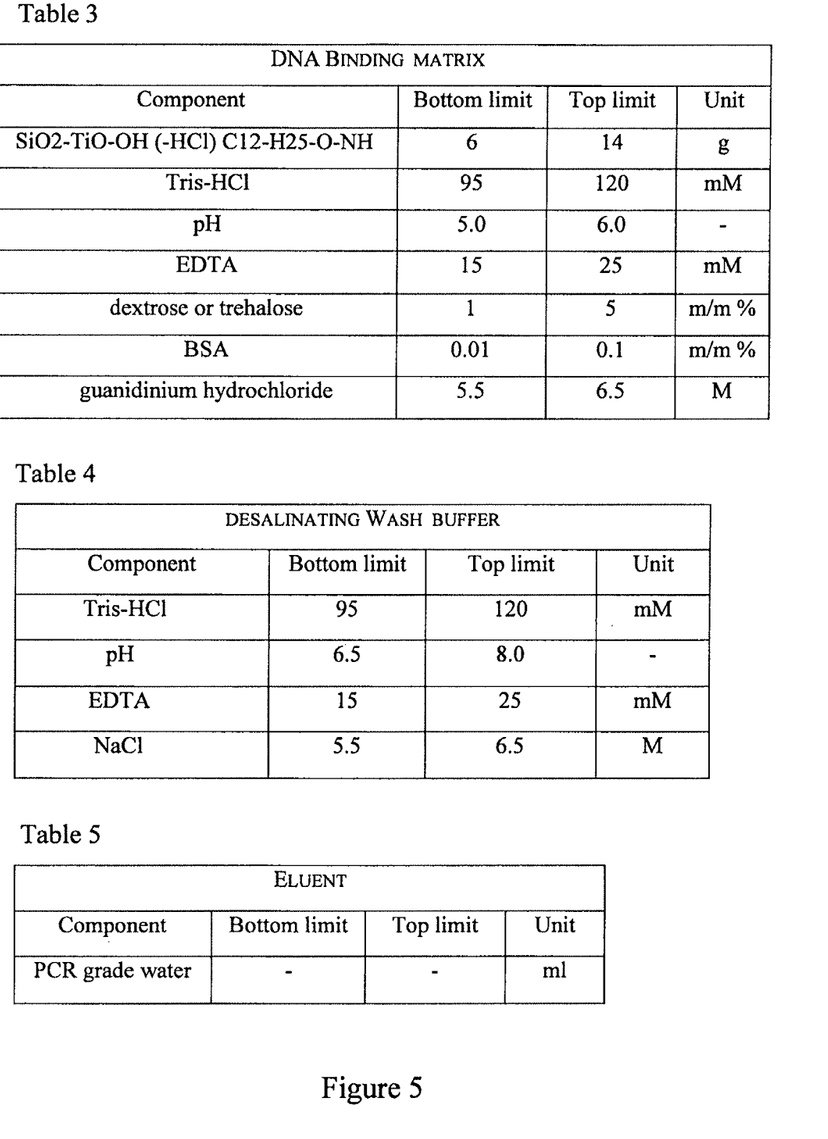
FIG. 5 shows compositions of a DNA binding matrix (Table 3), desalinating wash buffer (Table 4) and eluent (Table 5)

FIGS. 4 and 5. Tables 1-5 contain details of the possible realisation conditions of the procedure according to the invention, such as the components and pH ranges of the buffer removing nonviable cells, the lysis buffer, the binding matrix, the desalinating-wash buffer and the eluent.

Figure 6:
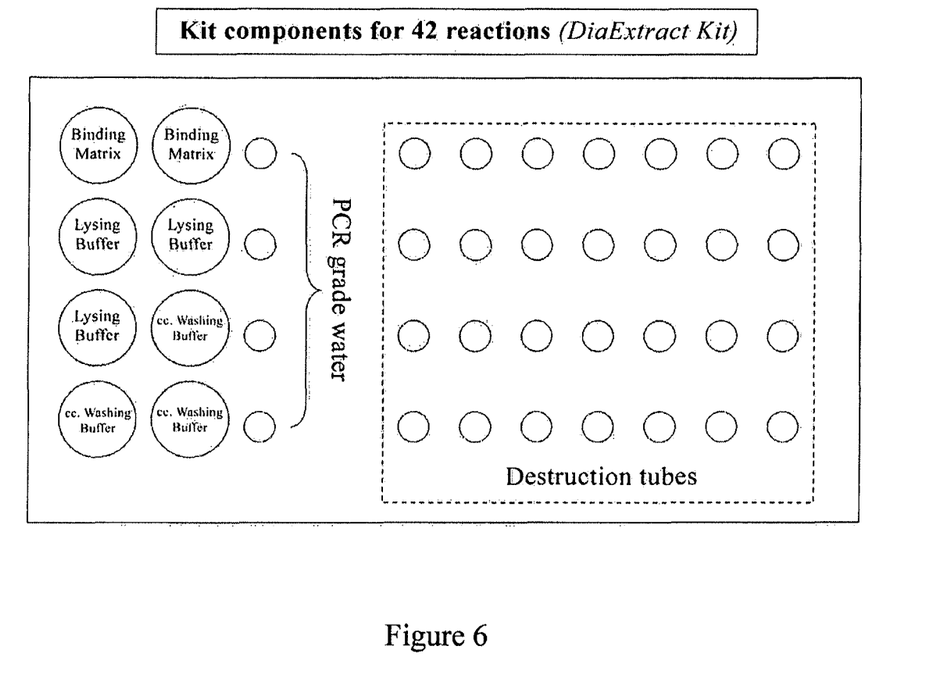
FIG. 6 is a schematic representation of a kit for isolation of total DNA content of bacteria in accordance with the present invention.

FIG. 6. Composition of the KIT for the specific isolation of total DNA content of bacterial germs. The kit shown is for processing 42 samples. In the figure a complex integral isolating system for microbial DNA isolations can be seen. The KIT contains the solutions used in the procedural steps following the removal of nonviable cells, such as the lysis buffer, the binding matrix, the desalinating-wash buffer and the eluent, as well as the destruction tubes described in the example of use and set up to suit current demands.

Below we summarise the advantages of the possible realisations of our invention. In the course of realisation favourably the guiding of the tables of FIGS. 4 and 5 listed below should be followed.

1) Table 1 shows the favourable composition of the buffered wash solution suitable for the separation of viable and nonviable cells according to our invention. As a result of the separation of viable and nonviable cells we enable the isolation of total DNA content exclusively from the viable cells of public health hygiene samples.
2) In the lysis buffer according to table 2 containing reducing dithiothreitol (DTT), anionic sodium dodecyl sulphate (SDS) and non-ionic detergent [TRITON X-100 (octylphenol ethoxylate)], in an alkaline Tris-HCl buffer environment, in the presence of divalent ion chelator (EDTA), unlike ordinary lysis buffers, the integrity of DNA in the disrupted bacterial cells is very favourably maintained.
   If the lysis buffer according to our invention is combined with a destruction tube prepared by us containing glass filings and steel ball, a disruption method is created, which can be adapted to automated DNA preparation and sample treatment system based on mechanical destruction.
3) The lysis buffer described in point 2 can also be efficiently combined with traditional disruption performed with lysozyme.
4) With the mixture of the components shown in table 3 we developed a DNA binding carrier matrix, with which DNA is bound directly after bacterial cell lysis in a sufficiently high extent, in an order of magnitude above 20 μg/100 mg binding capacity.
   The DNA binding surface according to our procedure is a —$SiO_2$—$TiO_2$— matrix containing chemically activated —OH and dodecylamine groups, favourably cross-linked with dodecylamine linkers, which matrix binds double-stranded DNAs selectively and exclusively in the environment according to table 3 and definitely does not bind the most common PCR inhibitors deriving from biological samples (e.g. porphyrins, bilirubin). On the matrix nonspecific secondary links (RNAs, proteins, other macromolecules) are blocked by adding trehalose or dextran, and BSA.
   According to our experience, denaturating chaotropic component guanidinium hydrochloride proved to be favourable.
5) With our desalinating wash buffer according to table 4 the contamination from DNA bound on the surface of DNA-binding carrier matrix is removed easily in the presence of bivalent ion chelator, in two washing steps, with short centrifugation periods.
6) The DNA bound on the DNA-binding carrier matrix surface according to table 3 and treated with our desalinating-wash buffer according to table 4 is eluted from the binding surface with PCR grade water according to table 5.
7) The average value characteristic of the purity of DNA eluted according to point 6 is:

$OD_{260}/OD_{280}=1.8$

The combined CV value characteristic of purity between two independent isolations performed with our procedure is: 9%
   The average concentration of DNA eluted according to point 6 is 60 μg/ml, the characteristic combined CV value is: 7.5%
   The average fragmentation of the DNA eluted according to point 6 is 5-12 kilobases (kb), the characteristic combined CV value is: 15%

The lowest initial bacterial germ number for DNA isolation performed with our procedure according to the invention is: $10^4$ CFU/ml, the characteristic combined CV value is: 10.5%

8) The amount of total DNA isolated from different germ number titers with the help of DNA-binding carrier matrix can be appropriately analysed by semiquantitative detection (see FIG. 3 and its explanation). In the course of semiquantitative detection first the DNA free from inhibitors, eluted from the matrix surface is entered into a PCR reaction, then the multiplied polynucleotide is detected in conventional agarose gel electrophoresis, with fluorescent density emitted by DNA intercalating stain ethidium bromide under UV exposure (see description).

9) A further special feature of our procedure is that the size of the bacterial DNA that can be prepared is minimum 500-1500 base pairs (bp) of linear polymer nucleic acid, and the use of our procedure for the preparation of DNA smaller than this is not favourable.

A further advantage of our procedure is that the physical-chemical maintenance of the extracted DNA, its purity and concentration make it suitable for use in downstream PCR applications.

A further advantage of our invention is that it can be realised quickly, and it can be combined with traditional and alternative extraction methods with the help of the lysis buffer prepared for this purpose.

A few of the possible realisations according to the invention are described below without restricting our scope of protection to these examples.

Examples of Realisation

Ideal opportunities for the isolation of total DNA content of bacterial germs in samples of water, food, clinical samples, solid and liquid environmental samples, as well as liquid-trapped air samples, etc.

In the course of realisation favourably the guiding of the tables of FIGS. 4 and 5 listed below should be followed.

A/ Sample Disruption with Mechanical and Enzymatic Treatment

Reaction optimised for general molecular biology laboratory instruments and isolating devices (e.g. FastPrep™)

First phase of the procedure/Removal of nonviable bacterial cells from the sample 1. The liquid cultured bacterial sample is sedimented at room temperature (RT), 10 min.
2. The liquid phase of the sample is transferred into a clean, sterile centrifuge tube.
3. The transferred sample is centrifuged: 3.000 rpm, 1 min., 25° C.
4. The supernatant is removed, then the sediment is thoroughly suspended in 5 ml of BUFFER REMOVING NONVIABLE CELLS (for its composition and pH see table 1).
5. The suspension is thoroughly mixed with a Vortex mixer.
6. The suspension is centrifuged: 3.000 rpm, 1 min., 25° C.
7. The supernatant is removed, then the precipitate is thoroughly suspended in 5 ml of BUFFER REMOVING NONVIABLE CELLS (for its composition and pH see table 1).
8. The suspension is thoroughly mixed with a Vortex mixer.
9. The suspension is centrifuged: 2.000 rpm, 1 min., 25° C.
10. The supernatant is removed, then the sediment is thoroughly suspended in 1 ml of BUFFER REMOVING NONVIABLE CELLS (for its composition and pH see table 1).
11. The suspension is thoroughly mixed with a Vortex mixer.
12. The suspension is centrifuged: 1.000 rpm, 3 min., 4° C.
13. The sediment is redissolved in 0.2-0.5 ml 0.1 M Tris-HCl (pH=7.5) buffer.
14. The sample is ready for cell lysis.

The compulsory characteristic features of the first phase of the procedure are the following:
a) Stock solutions are stored at +4° C.
b) When preparing stock solutions standard laboratory protocols relating to PCR procedures must be strictly followed (EN ISO 20838:2006, GLP).
c) Work in a strictly cleanroom environment (ISO 209, FS 209, BS5295, ISO 14644-1:1999), at a minimum safety level of BSL2 (Biosafety Level 2).

Second phase of the procedure/Cell lysis and double-stranded DNA binding on the carrier matrix surface 1. Transfer the sample treated according to steps 1-14 of the first phase of the procedure into a 2 ml destruction tube containing 0.1 g of glass filings and a CR-Va-steel ball of the size of 4.5" (4.5x25.4 mm).
2. Place the destruction tube containing the sample in a homogenising asymmetrical disruptor (e.g. FastPrep™), and then start cyclic disruption. After 30 seconds the sample can be passed on.
3. Add lysozyme enzyme to the sample at a final concentration of 100 μg/ml and incubate it for 15 minutes at 37° C. Then the sample can be passed on.
4. Add 1 ml of LYSIS BUFFER (composition and pH according to table 2) to the mechanically and enzymatically treated sample. Keep at room temperature for 1-2 minutes.
5. Centrifuge the suspension: 13.000 rpm, 5 min., 4° C.
6. Transfer 800 μl of the supernatant into a clean sterile 2.5 ml centrifuge tube.
7. Add 800 μl DNA BINDING MATRIX (composition and pH according to table 3). Close the centrifuge tube.
8. Carefully rotate the suspension 10-15 times. In this step do not use a vortex mixer by any means.
9. Incubate it for 2 minutes at room temperature, slowly rotating the tube at wide intervals.
10. Centrifuge the suspension: 12.000 rpm, 1 min. Remove the supernatant.
11. Suspend the precipitate in 700 μl of DESALINATING WASH BUFFER (composition and pH according to table 4).
12. Centrifuge the suspension: 12.000 rpm, 1 min. Remove the supernatant.
13. Suspend the precipitate in 500 μl of DESALINATING WASH BUFFER (composition and pH according to table 4).
14. Centrifuge the suspension: 12.000 rpm, 30 sec. Remove the supernatant.
15. Remove the residual supernatant above the precipitate carefully, without touching or stirring the matrix.
16. Allow the matrix to dry: 2 min., 37° C.
17. Add 100-120 μl of ELUENT (see table 5) to the dry matrix precipitate. Suspend the precipitate.
18. Leave it to stand at room temperature, 1 min.
19. Centrifuge: 12.000 rpm, 1 min.

20. Transfer the supernatant into a clean sterile DNase-free centrifuge tube.
21. The isolated DNA is ready for downstream applications.

The compulsory characteristic features of the second phase of the procedure are the following:
 a) Solutions and components are stored at +4 ... +8°C., with the exception of DNA BINDING MATRIX, which is kept at room temperature.
 b) When preparing stock solutions, the standard laboratory protocols relating to PCR procedures must be strictly followed (EN ISO 20838:2006, GLP).
 c) Work in a strictly cleanroom environment (ISO 209, FS 209, BS5295, ISO 14644-1:1999), at a minimum safety level of BSL2 (Biosafety Level 2).

Third phase of the procedure/Quantity and quality control

The concentration of isolated DNA is determined by the conventional laboratory technique of UV spectrophotometry, at a wavelength of $\lambda=260$ nm. The purity of the isolated DNA is characterised by the ratio of optical density values measured at wavelengths of $\lambda=260$ nm and $\lambda=280$ nm.

The compulsory characteristic features of the third phase of the procedure are the following:
 a) During the spectrophotometry procedure strictly follow the standard laboratory protocols relating to PCR procedures (EN ISO 20838:2006, GLP).
 b) Work in a strictly cleanroom environment (ISO 209, FS 209, BS5295, ISO 14644-1:1999), at a minimum safety level of BSL2 (Biosafety Level 2).

B/ Sample Disruption with Mechanical Treatment

Reaction optimised for general molecular biology laboratory instruments and isolating devices (e.g. FastPrep™)

First phase of the procedure/Removal of nonviable bacterial cells from the sample The steps and compulsory characteristic features of the procedure are the same as the ones described in the first phase of sample disruption A.

Second phase of the procedure/Cell lysis and double-stranded DNA binding on the carrier matrix surface 1) Transfer the sample treated according to steps 1-14 of the first phase of the procedure into a 2 ml destruction tube containing 0.1 g of glass filings and a CR-Va-steel ball of the size of 4.5" (4.5×25.4 mm).
2) Place the destruction tube containing the sample in a homogenising asymmetrical disruptor (e.g. FastPrep™), and then start cyclic disruption. After 30 seconds the sample can be passed on.
3) Add 1 ml LYSIS BUFFER (composition and pH according to table 2) to the mechanically treated sample. Keep at room temperature for 1-2 minutes.
4) Centrifuge the suspension: 13.000 rpm, 5 min., 4°C.
5) Transfer 800 µl of the supernatant into a clean sterile 2.5 ml centrifuge tube.
6) Add 800 µl DNA BINDING MATRIX (composition and pH according to table 3). Close the centrifuging tube.
7) Carefully rotate the suspension 10-15 times. In this step do not use a vortex mixer by any means.
8) Incubate it for 2 minutes at room temperature, slowly rotating the tube at wide intervals.
9) Centrifuge the suspension: 12.000 rpm, 1 min. Remove the supernatant.
10) Suspend the precipitate in 700 µl of DESALINATING WASH BUFFER (composition and pH according to table 4).
11) Centrifuge the suspension: 12.000 rpm, 1 min. Remove the supernatant.
12) Suspend the precipitate in 500 µl of DESALINATING-WASH BUFFER (composition and pH according to table 4).
13) Centrifuge the suspension: 12.000 rpm, 30 sec. Remove the supernatant.
14) Remove the residual supernatant above the precipitate carefully, without touching or stirring the matrix.
15) Allow the matrix to dry: 2 min., 37°C.
16) Add 100-120 µl of ELUENT (see table 5) to the dry matrix precipitate. Suspend the precipitate.
17) Leave it to stand at room temperature, 1 min.
18) Centrifuge: 12.000 rpm, 1 min.
19) Transfer the supernatant into a clean sterile DNase-free centrifuge tube.
20) The isolated DNA is ready for downstream applications.

The compulsory characteristic features of the second phase of the procedure are the following:
 a) Solutions and components are stored at +4 ... +8°C., with the exception of DNA BINDING MATRIX, which is kept at room temperature.
 b) When preparing stock solutions, the standard laboratory protocols relating to PCR procedures must be strictly followed (EN ISO 20838:2006, GLP).
 c) Work in a strictly cleanroom environment (ISO 209, FS 209, BS5295, ISO 14644-1:1999), at a minimum safety level of BSL2 (Biosafety Level 2).

Third Phase of the Procedure/Quantity and Quality Control

The concentration of isolated DNA is determined by the conventional laboratory technique of UV spectrophotometry, at a wavelength of $\lambda=260$ nm. The purity of the isolated DNA is characterised by the ratio of optical density values measured at wavelengths of $\lambda=260$ nm and $\lambda=280$ nm.

The compulsory characteristic features of the third phase of the procedure are the following:
 a) During the spectrophotometry procedure strictly following the standard laboratory protocols relating to PCR procedures (EN ISO 20838:2006, GLP).
 b) Work in a strictly cleanroom environment (ISO 209, FS 209, BS5295, ISO 14644-1:1999), at a minimum safety level of BSL2 (Biosafety Level 2).

C/ Sample Disruption with Enzymatic Lysis

Reaction optimised for general molecular biology laboratory instruments.

First phase of the procedure/Removal of nonviable bacterial cells from the sample The steps and compulsory characteristic features of the procedure are the same as the ones described in the first phase of sample disruption A.

Second phase of the procedure/Cell lysis and double-stranded DNA binding on the carrier matrix surface 1. Add lysozyme enzyme to the sample treated according to steps 1-14 of the first phase of the procedure, at a final concentration of 100 pg/ml and incubate it for 15 minutes at 37° C. Then the sample can be passed on.
2. Add 1 ml LYSIS BUFFER to the enzymatically treated sample (composition and pH according to table 2). Keep at room temperature for 1-2 minutes.
3. Centrifuge the suspension: 13.000 rpm, 5 min., 4° C.
4. Transfer 800 µl of the supernatant into a clean sterile 2.5 ml centrifuge tube.

5. Add 800 μl DNA BINDING MATRIX (composition and pH according to table 3). Close the centrifuging tube.
6. Carefully rotate the suspension 10-15 times. In this step do not use a vortex mixer by any means.
7. Incubate it for 2 minutes at room temperature, slowly rotating the tube at wide intervals.
8. Centrifuge the suspension: 12.000 rpm, 1 min. Remove the supernatant.
9. Suspend the precipitate in 700 μl of DESALINATING WASH BUFFER (composition and pH according to table 4).
10. Centrifuge the suspension: 12.000 rpm, 1 min. Remove the supernatant.
11. Suspend the precipitate in 500 μl of DESALINATING WASH BUFFER (composition and pH according to table 4).
12. Centrifuge the suspension: 12.000 rpm, 30 sec. Remove the supernatant.
13. Remove the residual supernatant above the precipitate carefully, without touching or stirring the matrix.
14. Allow the matrix to dry: 2 min., 37° C.
15. Add 100-120 μl of ELUENT (see table 5) to the dry matrix precipitate. Suspend the precipitate.
16. Leave it to stand at room temperature, 1 min.
17. Centrifuge: 12.000 rpm, 1 min.
18. Transfer the supernatant into a clean sterile DNase-free centrifuge tube.
19. The isolated DNA is ready for downstream applications.

The compulsory characteristic features of the second phase of the procedure are the following:
  a) The solutions and components are stored at +4 . . . +8° C., with the exception of DNA BINDING MATRIX, which is kept at room temperature.
  b) When preparing stock solutions, standard laboratory protocols relating to PCR procedures must be strictly followed (EN ISO 20838:2006, GLP).
  c) Work in a strictly cleanroom environment (ISO 209, FS 209, BS5295, ISO 14644-1:1999), at a minimum safety level of BSL2 (Biosafety Level 2).

Third phase of the procedure/Quantity and quality control
The concentration of isolated DNA is determined by the conventional laboratory technique of UV spectrophotometry, at a wavelength of $\lambda=260$ nm. The purity of the isolated DNA is characterised by the ratio of optical density values measured at wavelengths of $\lambda=260$ nm and $\lambda=280$ nm.
The compulsory characteristic features of the third phase of the procedure are the following:
  a) During the spectrophotometry procedure strictly follow the standard laboratory protocols relating to PCR procedures (EN ISO 20838:2006, GLP).
  b) Work in a strictly cleanroom environment (ISO 209, FS 209, BS5295, ISO 14644-1:1999), at a minimum safety level of BSL2 (Biosafety Level 2).

For the realisation of the steps of the procedure described in the examples of realisation the use of the following devices is favourable: BSL2 Class II Type A2 laminar cabinet, vortex mixer, refrigerated laboratory centrifuge and refrigerated microcentrifuge, 2 ml tube incubator, maybe water bath. Optionally a mechanical disruptor supporting automated disruption can be used (e.g. FastPrep™, TeenPrep™, BigPrep™, etc.).

One of the technical advantages of our invention is represented by good measuring technology parameters. According to this, between two independent isolations the combined variance (CV %) value characterising purity is low, 7.5-8.5% in the case of $10^6$ CFU/ml of bacterial colony. The specificity of the isolation is 95%, the reliability of reproducibility is 85%. The dynamic range of our double-stranded DNA isolation procedure is $10^4$-$10^8$ CFU/ml (100 mg sample) of bacterial colony.

Another technical advantage of our intention is its sensitivity: the minimal cell demand of DNA isolation, that is the absolute value of the bottom limit of the applicability of our method is $10^4$ CFU/ml±15%.

The third advantage of our invention is its fastness, which means that following the fast removal of nonviable cells total DNA content of bacterial germs can be isolated within about half an hour.

Among the economic advantages of our invention first of all fastness is mentioned again. After the fast removal of the nonviable cells, DNA isolation lasting for about half an hour provides a quick result in downstream applications of public health hygiene monitoring, such as in PCR analysis, which, if necessary, induces an intervention in due time at companies operating according to a quality control system (waterworks, food processing plants). As a result of this, no time is lost due to the shortness of the time required for product issues and control tests, or for the necessary withdrawal of a product.

The users and areas of application of our procedure for the isolation of bacterial germ total DNA content are drinking water, wastewater, public health bacteriological and waterworks testing laboratories, food testing stations, food industry test laboratories, general bacteriological laboratories, workplace hygiene and industrial and public hygiene laboratories.

A possible version of the commercial construction example of the KIT for the practical realisation of DNA isolation procedure according to the invention can be seen in FIG. 5. In the figure a complex integral isolating system for microbial DNA isolations can be seen. The KIT contains the solutions used in the procedural steps following the removal of nonviable cells (lysis buffer, binding matrix, desalinating wash buffer, eluent), as well as the destruction tubes described in the example of use.

We claim:
1. A kit for isolating DNA content of bacteria which comprises a lysing buffer, a —$SiO_2$—$TiO_2$— binding matrix of the formula $SiO_2$—$TiO$—$OH$(—$HCl$)$C_{12}H_{25}$—$O$—$NH$, a washing buffer, PCR grade water, and cell destruction tubes.
2. The kit in accordance with claim 1 wherein the lysing buffer has a pH value in the range of 6.5 to 8 and comprises dithiothreitol (DTT), ethylenediaminetetraacetic acid (EDTA), a non-ionic detergent, sodium dodecyl sulphate (SDS), Tris-HCl and sodium chloride.
3. The kit in accordance with claim 2 wherein the non-ionic detergent is octylphenol ethoxylate.
4. The kit in accordance with claim 1 wherein the binding matrix has a pH value in the range of 5 to 6 and further includes Tris-HCl, ethylenediaminetetraacetic acid, a polysaccharide which is a member of the group consisting of dextrose and trehalose, bovine serum albumin (BSA), and guanidinium hydrochloride.
5. The kit in accordance with claim 1 wherein the washing buffer has a pH value in the range of 6.5 to 8 and comprises Tris-HCl, ethylenediaminetetraacetic acid, and sodium chloride.

* * * * *